United States Patent [19]

Satoh

[11] Patent Number: 4,870,954

[45] Date of Patent: Oct. 3, 1989

[54] ULTRASONIC DIAGNOSTIC APPARATUS HAVING PIVOTABLE AND SLIDABLE OPERATIONAL TABLE

[75] Inventor: Tomohiro Satoh, Ootawara, Japan

[73] Assignee: Kabushiki Kaisha Toshiba, Kawasaki, Japan

[21] Appl. No.: 208,480

[22] Filed: Jun. 20, 1988

[30] Foreign Application Priority Data

Jun. 22, 1987 [JP] Japan ................................. 62-156348

[51] Int. Cl.⁴ ............................................ A61B 10/00
[52] U.S. Cl. .............................. 128/24 A; 128/660.07;
108/140; 312/322
[58] Field of Search ...................... 128/24 A, 845, 897,
128/660.07, 660.01; 312/322, 310; 108/26, 140,
143

[56] References Cited

U.S. PATENT DOCUMENTS

| | | | |
|---|---|---|---|
| 2,650,871 | 9/1953 | Holderegger | 312/322 |
| 3,271,020 | 9/1966 | Dlouhy et al. | 108/26 |
| 3,320,800 | 5/1967 | Harvey | 312/322 |
| 3,467,455 | 9/1969 | Caldemeyer | 312/322 |
| 3,547,101 | 12/1970 | Rosauer | 128/660.07 |
| 3,735,755 | 5/1973 | Eggleton et al. | 128/24 A |
| 3,837,720 | 9/1974 | Boris et al. | 108/26 |
| 4,058,001 | 11/1977 | Waxman | 128/660.07 |
| 4,274,685 | 6/1981 | Bradshaw | 312/322 |
| 4,379,429 | 4/1983 | Gubbe et al. | 108/143 |
| 4,483,572 | 11/1984 | Story | 312/322 |
| 4,515,086 | 5/1985 | Kwiecinsky et al. | 108/143 |
| 4,625,731 | 12/1986 | Quedens et al. | 128/660.07 |
| 4,643,547 | 2/1987 | Collins et al. | 108/140 |

FOREIGN PATENT DOCUMENTS

| | | | |
|---|---|---|---|
| 2511735 | 9/1976 | Fed. Rep. of Germany | 108/26 |
| 2302079 | 10/1976 | France | 108/140 |
| 63-9429 | 1/1988 | Japan . | |

Primary Examiner—Edgar S. Burr
Assistant Examiner—Tonga Lamb
Attorney, Agent, or Firm—Cushman, Darby & Cushman

[57] ABSTRACT

A ultrasonically diagnostic apparatus including a ultrasonically diagnostic body for obtaining ultrasonic information, in which an operational table arranged in front of the body is rotatably supported by a pivotally supporting device which is slidably supported by a slidably supporting device secured to a front side of the body, and thus the operational table is pivotal in left and right hand side directions and also slidable frontwards and rearwards.

10 Claims, 4 Drawing Sheets

ULTRASONIC DIAGNOSTIC APPARATUS HAVING PIVOTABLE AND SLIDABLE OPERATIONAL TABLE

BACKGROUND OF THE INVENTION

1. Field of the Invention

The present invention relates to an ultrasonic diagnostic apparatus for obtaining ultrasonic information of a subject.

2. Description of the Prior Art

In a conventional ultrasonic diagnostic apparatus, an operational table for inputting necessary information by an operator such as a doctor is mounted to an operational front side in an approximately horizontal state.

When the necessary information is input to the operational table, the operator conducts the operation while sitting on a chair or standing. However, in the conventional ultrasonic diagnostic apparatus, when the operator carries out the operation while sitting on the chair, the knees of the operator often contact the operational front side or various instruments or devices such as a recorder arranged thereby, and hence an operational range of the operational table becomes narrow, with the result of poor and inconvenient operational efficiency. Further, the height of the operational table is designed to adapt to both the sitting and standing operations. Accordingly, when the operator conducts the operation while sitting on the chair, the height of the operational table is higher and it is inconvenient for the operator.

Further, a bed for supporting a subject is usually arranged by the right or left side of the diagnostic apparatus, and thus the operator takes up his position in proximity to the bed so as to conduct the detection operation. That is, the operator cannot take up his position to the front of the operational table, and, when he inputs the information into the operational table, he must shift his body towards the operational table in order to operate the diagnostic apparatus in an easy and proper manner.

SUMMARY OF THE INVENTION

Accordingly, it is an object of the present invention to provide an ultrasonic diagnostic apparatus, free from the aforementioned inconveniences and defects of the prior art, which is capable of improving the operational efficiency of the apparatus.

In accordance with one aspect of the present invention, there is provided an ultrasonic diagnostic apparatus comprising an ultrasonic diagnostic body for obtaining ultrasonic information, an operational table arranged in front of the body, means for pivotally supporting the table and means for slidably supporting the pivotally supporting means, the slidably supporting means being secured to a front side of the body, the pivotally supporting means being slidable frontwards and rearwards.

BRIEF DESCRIPTION OF THE DRAWINGS

The above object and other objects, features and advantages of the present invention will more fully appear from the following description of the preferred embodiments with reference to the accompanying drawings, in which.

DESCRIPTION OF THE PREFERRED EMBODIMENTS

Figure 1:
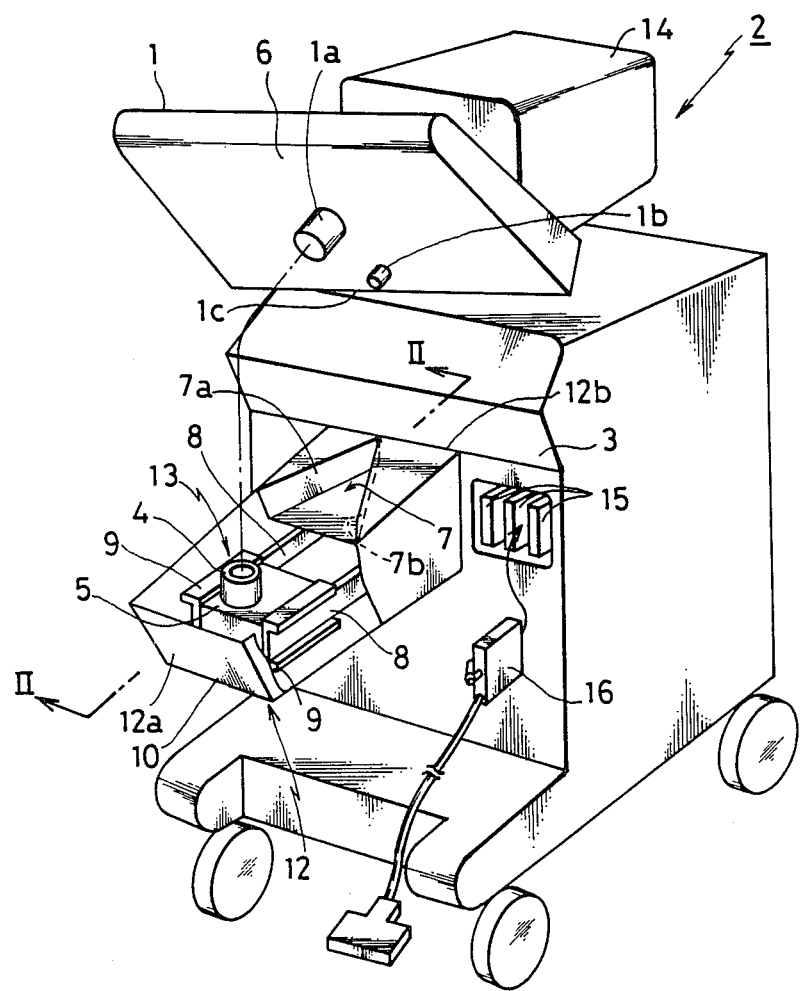
FIG. 1 is a perspective view of one embodiment of an ultrasonic diagnostic apparatus according to the present invention.
Figure 2A:
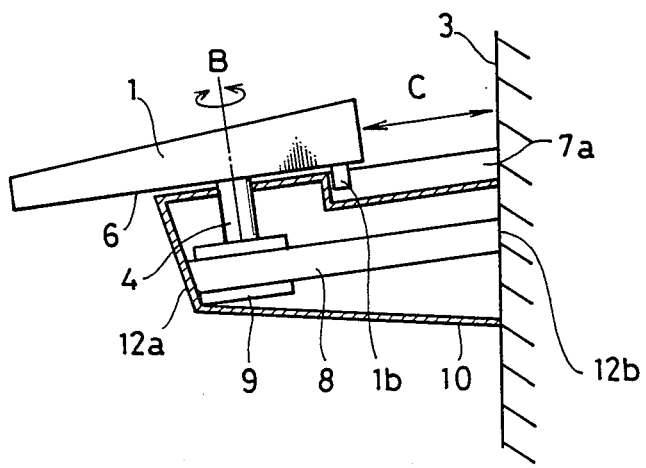
FIG. 2a is a longitudinal cross sectional view, taken along the line II—II of FIG. 1, in which an operational table is drawn up forwards
Figure 2B:
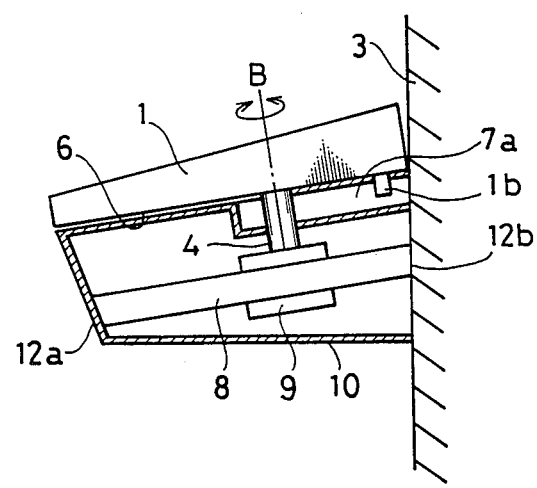
FIG. 2b is a similar view to FIG. 2a, in which the operational table is not drawn up forwards.
Figure 3:
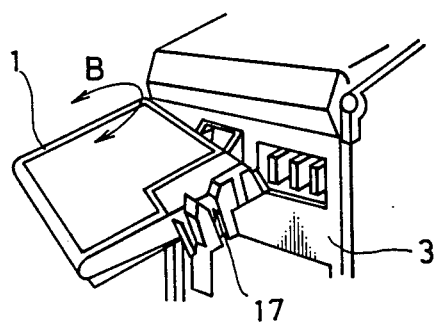
FIG. 3 is a fragmentary perspective view of the operational table rotated in the clockwise direction.

Referring now to the drawings, wherein like reference characters designate like or corresponding parts throughout the several views, there is shown in FIGS. 1 through 3 one embodiment of an ultrasonic diagnostic apparatus according to the present invention.

In the drawings, the ultrasonic diagnostic apparatus includes an ultrasonic diagnostic body 2 for obtaining ultrasonic information and an operational table 1 having a plurality of keys arranged thereon on an operational front side 3 of the body 2. The diagnostic apparatus also includes a rotatably supporting part 13 having a cylindrical rotary bearing member 4 on its upper surface for rotatably supporting the operational table 1, and a slidably supporting part 12 for slidably supporting the rotatably supporting part 13. The slidably supporting part 12 projects frontwards from about the middle of the operational front side 3 of the body 2 at a proper height.

A color display 14 such as a CRT is disposed onto the top of the body 2, and connector terminals 15 for coupling with connectors 16, connected to other instruments or devices (not shown) such as a recorder and the like via wires, are provided to the right hand side of the front side 3 of the body 2 below the operational table 1.

The operational table 1 is provided with a rotary shaft 1a on the bottom 6 with the shaft projecting downwards from approximately its central portion of its bottom and a stopper pin 1b projecting downwards from a central rear portion of the bottom in close proximity to a rear end 1c of the operational table 1.

The slidably supporting part 12 includes a pair of slide rails 8 arranged in parallel a certain distance away from each other. The rear ends of the slide rails 8 are so secured to the front side 3 of the body 2 that the rails 8 may be inclined and the front ends of the rails 8 may be lower than the rear ends thereof, as shown in FIGS. 2a and 2b. The slidably supporting part 12 also includes the rotatably supporting part 13 which is slidable along the rails 8, as indicated by an arrow C of FIG. 2a, and a case 10 having front and rear ends 12a and 12b for containing the rails 8 and the rotatably supporting part 13. The rear end 12b of the case 10 is mounted to the front side 3 of the body 2 and an upper surface of the case 10 is also inclined in parallel with the rails 8.

The case 10 is provided with a stopper member 7 of a triangular groove shape having left and right stopper walls 7a and 7b in the rear half portion of the upper surface. One vertex of the triangular stopper member 7 is positioned in the upper middle portion of the rear end wall of the case 10 and two vertices of the triangular stopper member 7 are positioned in the upper portions of the left and right side walls of the case 10. The operational table 1 is rotatably mounted onto the rotatably supporting part 13 by fitting the rotary shaft 1a of the operational table 1 into the bearing member 4 of the rotatably supporting part 13. When the operational table 1 is pivoted, as indicated by an arrow B of FIGS. 2a and 2b, the stopper pin 1b of the operational table 1 is stopped by the left and right stopper walls 7a and 7b of the stopper member 7 so that the operational table 1 may not contact the front side 3 of the body 2. The stopper member 7 is not restricted to the triangular groove shape and to the structure described above, and, of course, other shapes and other structures may be used for the stopper member 7.

The rotatably supporting part 13 includes a mount member 5 having a cubic box form, the cylindrical rotary bearing member 4 secured upright to nearly the central portion of the upper surface of the mount member 5, and a pair of channel members 9 attached to both the sides of the mount member 5, for slidably holding the rails 8. In this case, instead of the cylindrical rotary bearing member 4, any device for rotatably supporting the operational table 1, for instance, a ball bearing can be used. Further, the device for rotatably supporting the operational table 1 may include a mechanism for intermittently stopping the rotational motion of the operational table 1, after a certain amount of angular movement, with accuracy. In addition, a device for locking the rotary shaft 1a of the operational table 1 in the cylindrical rotary bearing member 4 may be provided.

Further, as shown in FIG. 3, the operational table 1 is provided with a scope or probe holder 17 on its right hand side.

In this embodiment, when the operator carries out the operation while sitting at the operational table 1, as shown in FIG. 2a, the operational table 1 is drawn up forwards and the height of the operational table 1 is lowered with reference to that of the operational table 1, which is not drawn up, as shown in FIG. 2b, with the result of improving the operational efficiency. Further, when the operational table 1 is drawn up forwards, the operational table 1 is moved frontwards away from the front side 3 of the body 2 thus preventing contact between the knees of the operator and the front side 3.

Then, when the operator conducts the operation while standing, the operational table 1 may not be drawn up, as shown in FIG. 2b. In this case, the height of the operational table 1 is relatively high. Hence, good operational efficiency can be obtained during the standing operation.

As shown in FIGS. 1 to 3, since the slidably supporting part 12 slidably supports the rotatably supporting part 13, which rotatably supports the operational table 1, the operational table 1 can be pivoted on any position along the rails 8. Therefore, when a bed for supporting a subject to be detected is arranged in the right or left hand side of the body 2 and the operator positions close to the bed during the operation, the operational table 1 can be pivoted at a suitable angle in order to take up the operator's position to the front of the operational table 1 without shifting his body towards the operational table 1. Further, when the operational table 1 is pivoted in the counterclockwise direction, the connectors 16 for connecting the other instruments or device to the body 2 can be readily engaged or disengaged with or from the connector terminals 15 of the body 2.

Figure 4:
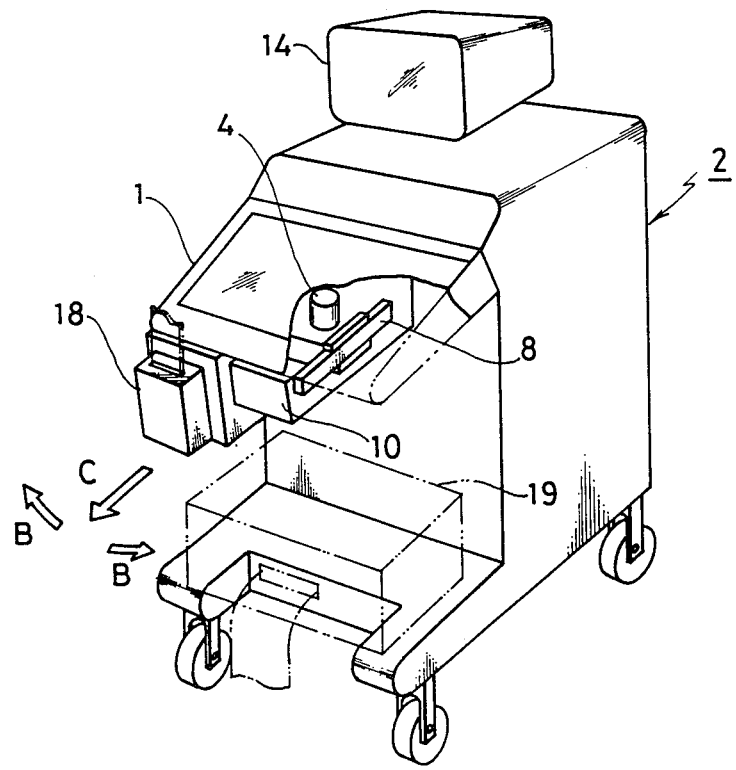
FIG. 4 is a perspective view of another embodiment of an ultrasonic diagnostic apparatus according to the present invention.

Next, in FIG. 4, there is shown another embodiment of an ultrasonic diagnostic apparatus according to the present invention having the same construction as that of the first embodiment shown in FIGS. 1 to 3, except that a photographing device 18, such as a camera for photographing a picture displayed on the display 14, is attached to the front end of the operational table 1. In this embodiment, since the photographing device 18 is moved with the operational table 1, the operator can readily operate the photographing device 18, for example, to push a shutter switch and to pull out film, as compared with a conventional ultrasonic diagnostic apparatus having a photographing device attached to its body under a table.

Further, in this embodiment, a recorder 19 such as a video cassette recorder (VCR) and a line scan recorder (LSR) can be suitably set in a space under the slidably supporting part 12 of the body 2.

Although the present invention has been described in its preferred embodiments with reference to the accompanying drawings, it is readily understood that the present invention is not restricted to the preferred embodiments and that various changes and modifications may be made in the present invention by a person skilled in the art without departing from the spirit and scope of the present invention.

Figure 5:
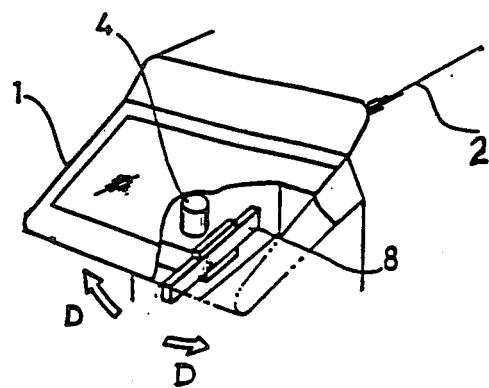

For instance, although the slide rails 8 are secured to the front side 3 of the body 2 at their rear ends 12 in the preferred embodiments, the slide rails 8 may be pivotally mounted to the front side 3 of the body 2 so as to pivot in the longitudinal direction, D, as shown in FIG. 5. In this case, of course, the same results as those obtained in the preferred embodiments described above can be obtained.

What is claimed is:

1. An ultasonic diagnostic apparatus, comprising:
an ultrasonic diagnostic body for obtaining ultrasonic information, the diagnostic body having a front;
an operational table having a pivot axis and arranged in front of the body;
means for pivotally supporting the table around the pivot axis;
means, connected to the pivotal means, for slidably supporting the pivotal support means, the slidable support means being secured to the front side of the body so the pivotal support means is slidable relative to the body to adjust the position of the table relative to the body; and
stopper means, mounted to the slidable support means, for gradually and variably restricting the pivotal movement of the table depending on the position of the table relative to the body to prevent the table from pivoting into contact with the body.

2. The apparatus of claim 1, wherein the slidably supporting means includes front and rear ends and is inclined so that the front end is lower than the rear end.

3. The apparatus of claim 1, wherein the body includes a case extending from the front of the body, the case having a triangular groove;
the table including a stopper pin;
the stopper means comprising the stopper pin inserted within the triangular groove.

4. An apparatus according to claim 1, wherein the operational table includes a scope holder.

5. An apparatus according to claim 1, wherein the slidably supporting means includes a pair of slide rails.

6. An apparatus according to claim 1, wherein the slidably supporting means is pivotally secured to the front side of the body.

7. An apparatus according to claim 1, wherein the operational table includes a camera.

8. An apparatus according to claim 7, wherein the table includes a front end, the camera being mounted to the front end.

9. An apparatus according to claim 1, wherein the operational table includes at least one of a VCR and an LSR.

10. An apparatus according to claim 9, wherein the at least one of a VCR and an LSR is mounted to the operational table below the slidably supporting means.

* * * * *